United States Patent
Mimura et al.

(10) Patent No.: US 6,544,476 B1
(45) Date of Patent: Apr. 8, 2003

(54) AUTOMATIC ANALYZER CAPABLE OF RESTRICTING USABLE OPERATION FUNCTIONS

(75) Inventors: Tomonori Mimura, Ibaraki-ken (JP); Taku Sakazume, Hitachinaka (JP); Atsushi Takahashi, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/294,433

(22) Filed: Apr. 20, 1999

(30) Foreign Application Priority Data

Apr. 21, 1998 (JP) ............................................ 10-110436

(51) Int. Cl.⁷ .......................... G01N 35/00; G06F 17/40
(52) U.S. Cl. .............................. 422/67; 422/63; 422/64; 422/68.1; 436/43; 436/47; 436/49; 700/266
(58) Field of Search ............................... 422/62, 63, 64, 422/67, 68.1, 82.05, 82.09; 436/43, 47, 49, 164; 700/266

(56) References Cited

U.S. PATENT DOCUMENTS

| | | | |
|---|---|---|---|
| 3,693,166 A | | 9/1972 | Rawson et al. |
| 4,857,716 A | | 8/1989 | Gombrich et al. |
| 4,873,633 A | | 10/1989 | Mezei et al. |
| 5,029,065 A | * | 7/1991 | Nau et al. .................... 364/146 |
| 5,068,798 A | * | 11/1991 | Heath et al. ................. 364/497 |
| 5,730,124 A | * | 3/1998 | Yamauchi ................... 128/630 |
| 5,730,939 A | * | 3/1998 | Kurumada et al. ............ 422/67 |
| 5,777,902 A | * | 7/1998 | Ono et al. ................... 364/579 |
| 6,036,856 A | * | 3/2000 | Ono et al. ................ 210/198.2 |
| 6,080,364 A | * | 6/2000 | Mimura et al. ................ 422/67 |
| 6,090,630 A | * | 7/2000 | Koakutsu et al. ............. 436/50 |

FOREIGN PATENT DOCUMENTS

| | | |
|---|---|---|
| DE | 195 01 531 | 9/1995 |
| EP | 684 575 | 11/1995 |
| EP | 871 034 A2 * | 8/1997 |
| JP | 1-250758 | 10/1989 |
| JP | 9-211003 | * 8/1997 |

* cited by examiner

Primary Examiner—Jill Warden
Assistant Examiner—Kathryn Bex
(74) Attorney, Agent, or Firm—Mattingly, Stanger & Malur, P.C.

(57) ABSTRACT

When the operation function of an automatic analyzer is allowed to use, all selection buttons respectively provided in corresponding to a plurality of operation functions being grouped are displayed on a predetermined area of a CRT display. In this case, the button corresponding to the operation function allowed to be used for a particular operator is indicated by the color representing accessible, while the button corresponding to the operation function not allowed to be used for the particular operator is indicated by the color representing not-accessible. When the button corresponding to the accessible operation function is selected, the subclass operation function screens relating to the selected operation function are displayed in a hierarchy fashion or a multi-layer fashion.

4 Claims, 6 Drawing Sheets

AUTOMATIC ANALYZER CAPABLE OF RESTRICTING USABLE OPERATION FUNCTIONS

BACKGROUND OF THE INVENTION

The present invention relates to an automatic analyzer for analyzing the inspection items of a sample and, more particularly, relates to an automatic analyzer capable of restricting the operation functions accessible to the automatic analyzer in accordance with the password of an operator.

The automatic analyzer serves to react the component (inspection item) contained in the biological sample solution of a patient such as blood (serum or plasma) or urine with the reagent to automatically measure the concentration of the component. The operation screen displayed on the user interface of the conventional automatic analyzer is same irrespective of an operator and the kind of work such as an urgent inspection in the nighttime, a routine work in the daytime or the like. Accordingly, in the case of the urgent inspection in the nighttime, for example, when a person who is not so familiar with the automatic analyzer like a nurse or a doctor is required to operate the automatic analyzer, it is difficult for such a person to operate the automatic analyzer. Further, there is a possibility that such an operator who is not so familiar with the automatic analyzer may erroneously operate the automatic analyzer.

In order to solve such a problem, J-P-A 1-250758 proposes that the operation level of an operator is determined and the operator is allowed to use only the particular range of the function corresponding to the determined level. In other words, the J-P-A 1-250758 discloses that the operation functions of the automatic analyzer are classified into an analysis parameter, a system parameter, registration and maintenance, and the levels of the operators are set in accordance with identification (ID) codes of the respective operators in advance, respectively. Accordingly, when an operator inputs the ID code, only the operation function of the operation level corresponding to the inputted ID code is displayed. The levels of the operator is set as three levels of upper, middle and lower levels in a manner that the operator of the upper level is allowed to operate all the operations, the operator of the middle level is allowed to operate a part of the operations, and the operator of the lower level is allowed to operate only a part of the analysis parameter and the maintenance.

The aforesaid J-P-A 1-250758 teaches that, in response to the input of the ID code of the operator, only the function corresponding to the inputted level of the operator is displayed. However, the prior art disclosed in the J-P-A 1-250758 does not teach the arrangement of the user interface suitable for an operator.

BRIEF SUMMARY OF THE INVENTION

An object of the present invention is to provide an automatic analyzer so arranged that an operator can look over the entire summary of the operation functions and easily select a plurality of operation function screens allowed to the operator.

Another object of the present invention is to provide an automatic analyzer so arranged that an operator having inputted a password is allowed to access to the operation function of higher level and an operator having inputted no password is allowed to access to the operation function required to the minimum for analyzing a sample.

The present invention is applied to an automatic analyzer which automatically analyzes a sample to obtain the concentration of an inspection item. The automatic analyzer includes a memory for storing information of operation functions divided into a plurality of groups, and a controller for determining a level corresponding to a password having been inputted and allowing an operator to access to the operation function of a particular group in accordance with the level thus determined.

An automatic analyzer according to the present invention further includes a display device for displaying a screen having an area for indicating operation function selection buttons corresponding to the respective groups of the operation functions divided into the plurality of groups and an area for indicating an operation function screen corresponding to selected one of the operation function selection buttons, wherein the controller controls one of the operation function selection buttons, which corresponds to the particular one of the plurality of groups allowed to access based on the level thus determined, to be accessible and also controls remaining one of the operation function selection buttons, which corresponds to remaining one of the plurality of groups having not been allowed to access, not to be accessible.

According to an example of the present invention, the one of the operation function selection buttons corresponding to the particular one of the plurality of groups allowed to access is displayed in different color from the remaining one of the operation function selection buttons corresponds to remaining one of the plurality of groups not allowed to access.

According to an example of the present invention, in a case where one of the operation function selection buttons corresponding to the particular one of the plurality of groups allowed to access is selected, when there is a plurality of operation function screens relating to the selected one of the operation function selection buttons, the plurality of operation function screens are displayed in a multi-layer fashion.

According to an example of the present invention, one of the plurality of operation function screens corresponding to the operation function of a lowest level is displayed on an uppermost layer.

According to an example of the present invention, when the password is not inputted after turning-on of a power source of the automatic analyzer, the controller controls in a manner that only one of the operation function selection buttons corresponding to the operation function necessary for urgent analysis of a sample to be accessible.

DETAILED DESCRIPTION OF THE INVENTION

The automatic analyzer according to an embodiment of the present invention will be explained with reference to the accompanying drawings 1 to 6. In this preferred embodiment, the automatic analyzer executes, in accordance with the contents inputted by means of the screen of an operation function being displayed, the analysis operation of a sample and displays the analysis result of the respective inspection items of the sample. The automatic analyzer includes a user interface so constructed that a beginner such as a doctor or a nurse who is not familiar with the operation of the automatic analyzer can operate without causing erroneous operation at the time of requiring an urgent inspection in the nighttime and further an operator such as a person in charge of the management of an analyzing room who is familiar with the operation of the automatic analyzer can easily operate the analyzer.

Figure 1:
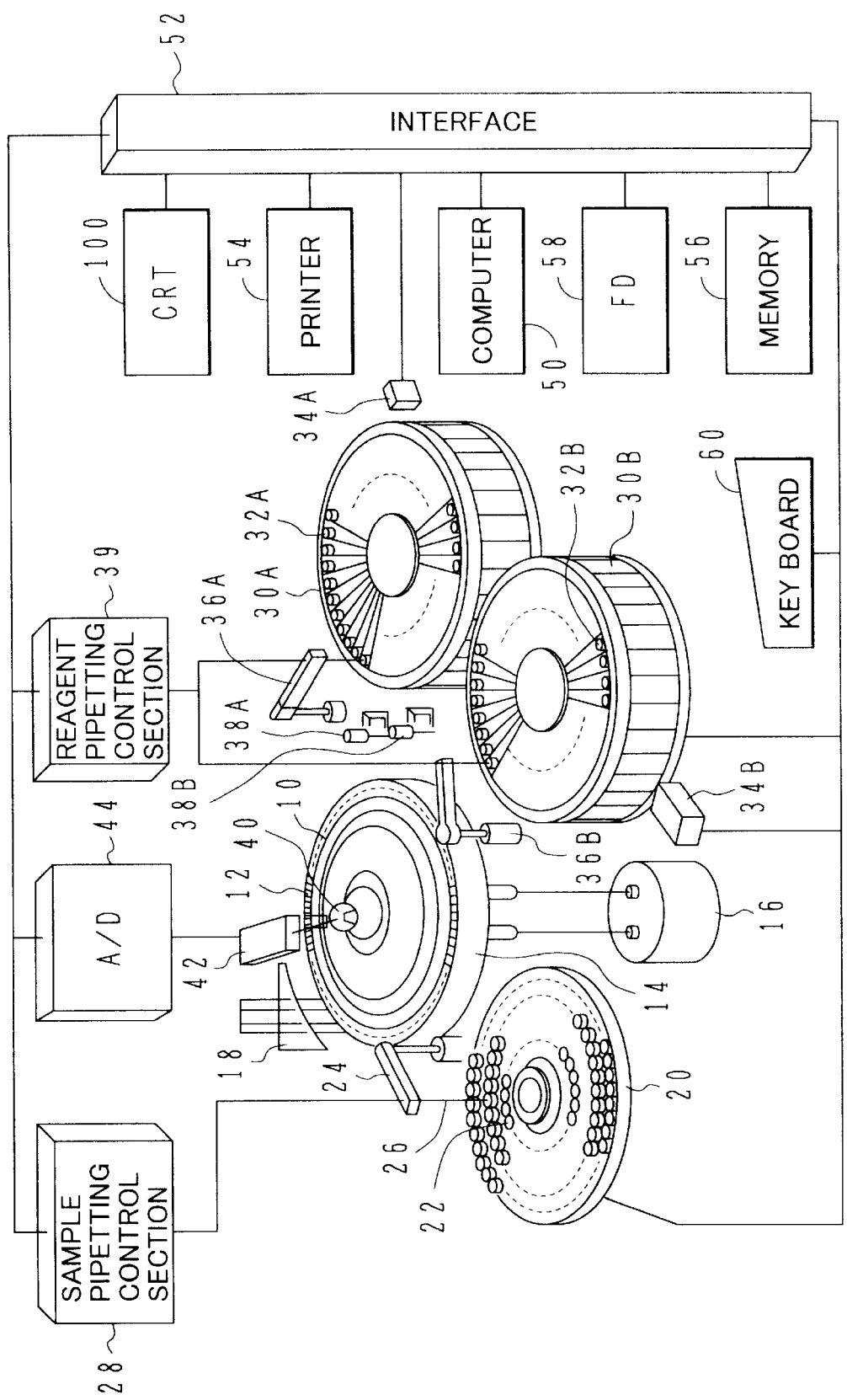
FIG. 1 is a schematic diagram showing the entire configuration of an automatic analyzer according to an embodiment of the present invention.

FIG. 1 shows the entire configuration of the automatic analyzer. A multiplicity of reaction containers 12 made of light transmission material are mounted along the circular periphery of a reaction disk 10 which is provided so as to be rotatable intermittently. The reaction containers 12 are maintained at a predetermined temperature (for example, 37 C) by means of a thermostat bath 14. The temperature of the fluid within the thermostat bath 14 is adjusted by a constant temperature maintenance device 16.

A multiplicity of sample cups 22 containing biological sample solution such as the blood or urine are placed on a sample disk 20. A pipette nozzle 26 attached to a movable arm 24 sucks a predetermined amount of sample from the sample cup 22 positioned at the suction position of the sample disk 20 and pipettes or discharges the sample thus sucked within the reaction container 12 positioned at the pipette position on the reaction disk 10.

A plurality of reagent bottles 32A, 32B, on each of which a label showing the reagent identification information such as a bar code is pasted, are placed on reagent disks disposed within the reagent cold reserving boxes 30A, 30B, respectively. Each of these reagent bottles contains reagent solution corresponding to the analysis item to be analyzed by the automatic analyzer. Each of bar code readers annexed to the reagent cold reserving boxes 30A, 30B reads bar codes indicated at the outer walls of the reagent bottles at the time of registration of the reagents. The reagent identification information thus read is stored in a memory 56 described later together with the positional information of the reagent bottles on the reagent disk.

The reagent pipette nozzles of the reagent pipetting mechanisms 36A, 36B suck reagent solution from the reagent bottles within the reagent cold reserving boxes 30A, 30B corresponding to the inspection items and pipette the reagent solution within the corresponding reaction containers 12 which are positioned at the reagent receiving positions on the reaction disk 10, respectively. The mixtures of the samples and the reagent solution within the reaction containers 12 are stirred by stirring mechanisms 38A, 38B, respectively.

A sequence of the reaction containers 12 are rotated so as to pass a light measurement position sandwiched between a white light source 40 and a multi-wavelength photometer 42. The light passed through the reaction solution of the sample and the reagent solution within each of the reaction containers 12 is measured during the rotation of the reaction disk 10. An analog signal thus obtained through the light measurement at every sample is inputted into an analog-to-digital (A/D) converter 44. A reaction container washing mechanism 18 disposed in the vicinity of the reaction disk 10 washes the insides of the reaction containers 12 having been subjected to the light measurement thereby to make it possible to use the reaction containers repeatedly.

The controller and the signal processing section in the automatic analyzer of FIG. 1 will be explained briefly. A computer 50 is connected to a sample pipetting control section 28, a reagent pipetting control section 39 and the A/D converter 44 through an interface 52. The computer 50 sends a command to the sample pipetting control section 28 thereby to control the pipetting operation of the sample. Further, the computer 50 sends a command to the reagent pipetting control section 39 thereby to control the pipetting operation of the reagent. The light measurement value is converted into a digital value by the A/D converter 44 and then taken into the computer 50.

The interface 52 is connected to a printer 54 for printing, the memory 56 serving as a storage device, a floppy disc drive device 58, a key board 60 for inputting an operation command or the like, and a CRT display 100 serving as a display device for displaying the screens. As the screen display device, a liquid crystal display or the like may be employed in place of the CRT display. The memory 56 is formed by a hard disc memory or an external memory, for example. The memory 56 stores information such as passwords of the respective operators, levels of the respective screens, analysis parameters, contents of the request for the analysis items, calibration results, analysis results, or the like.

The analyzing operation of the sample in the automatic analyzer of FIG. 1 will be explained. The analysis parameters relating to the items capable of being analyzed by the automatic analyzer are inputted through an information input device such as the key board 60 and stored in the memory 56. An operator selects the inspection item requested at every sample by using the operation function screen described later. In this case, the information such as a patient ID is also inputted from the key board 60. In order to analyze the inspection item instructed at every sample, the pipette nozzle 26 sucks a predetermined amount of the sample from the sample cup 22 and pipettes the sample thus sucked within the reaction container 12 in accordance with the analysis parameter. The reaction container 12 thus received the sample therein is transferred in accordance with the rotation of the reaction disk 10 and stopped at the reagent receiving position. The reagent pipette nozzles of the reagent pipetting mechanisms 36A, 36B suck predetermined amounts of reagent solution from the reagent bottles in accordance with the analysis parameter(s) of the inspection item(s) and pipette the reagent solution within the corresponding container(s) 12. The pipetting order between the sample and the reagent may not be limited to the aforesaid order and the reagent may be pipetted prior to the pipetting of the sample.

Thereafter, the mixtures of the samples and the reagent solution within the reaction containers 12 are stirred by the stirring mechanisms 38A, 38B, respectively. When the reaction container 12 passes through the light measurement position, the absorbance of the reaction solution within the reaction container 12 is measured by the multi-wavelength photometer 42. The absorbance thus measured is taken into the computer 50 through the A/D converter 44 and the interface 52. The absorbance is converted into component concentration data on the basis of the calibration curve which has been measured in advance by using the analysis method designated at every inspection item. The component concentration data representing the analysis results of the respective inspection items is outputted to the printer 54 and/or displayed on the CRT display 100.

Prior to the execution of the aforesaid measuring operation, an operator sets various kinds of parameters and registers the sample necessary for the analysis measurement. Further, the operator confirms the analysis result after the measurement by the operation screen displayed on the CRT display 100.

Figure 2:
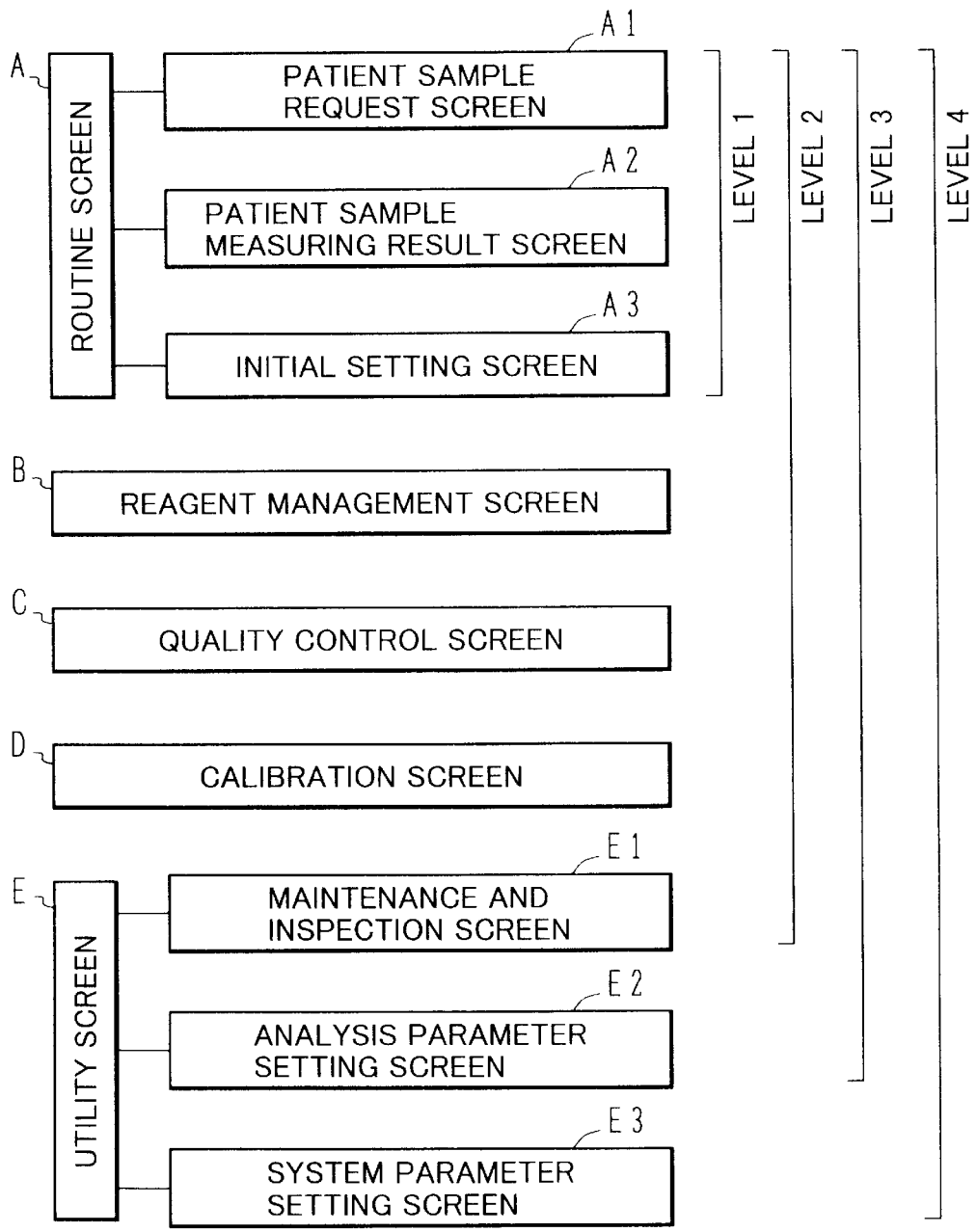
FIG. 2 is a diagram showing the relation between the kinds of the operation function screens being displayed on a CRT display of the automatic analyzer in FIG. 1 and the levels being allowed to an operator.

The relation between an example of the operation screens capable of being displayed on the CRT display of the automatic analyzer according to the embodiment and the respective levels will be explained with reference to FIG. 2. FIG. 2 shows the relation between the kinds of the operation screens capable of being displayed on the CRT display 100 and the levels being allowed to an operator. The operation functions relating to the automatic analyzer are divided into a plurality of groups as shown by A to E in FIG. 2. The information of these operation function screens are stored in the memory 56. The operation function screens are selectively displayed under the control of the computer 50.

As shown in FIG. 2, the screens corresponding to the entire operation functions of the automatic analyzer are classified into the five groups, that is, a routine screen A, a reagent management screen B, an quality control screen C, a calibration screen D and a utility screen E. The operation function(s) of each of these groups accepts an instruction through at least one operation function screen and the operation function thus instructed is executed under the control of the computer 50.

The routine screen A in FIG. 2 is formed by a patient sample request screen A1, a patient sample measuring result screen A2 and an initial setting screen A3. The utility screen E is formed by a maintenance and inspection screen E1, an analysis parameter setting screen E2 and a system parameter setting screen E3.

The contents of the respective screens will be explained.

The patient sample request screen A1 within the routine screen A is a screen for selecting an inspection item at every sample of each patient and registering the selected inspection item. The patient sample measuring result screen A2 is a screen for displaying the measured data of each patient so that an operator can confirm the measured data. The initial setting screen A3 is a screen for setting the condition and instructing the preparation operation for the automatic analyzer at the time of starting the analysis.

The reagent management screen B is a screen for confirming the remaining amounts of the reagents within the respective reagent bottles and registering new reagents. The quality control screen C is a screen for setting the condition for monitoring the abnormality of the measured data or the degradation states of the reagents and for displaying the monitored result. The calibration screen D is a setting screen for executing the calibration by reacting the reagent with the standard reagent or calibrator.

The maintenance and inspection screen E1 of the utility screen E is used at the time of setting the condition for executing the maintenance of the analyzer and used at the time of displaying the stored date representing the result of the periodical maintenance operation. The analysis parameter setting screen E2 is a screen for setting the parameter as the analysis condition to be stored as to the respective items capable of being analyzed. The system parameter setting screen E3 is a screen for setting the kinds of samples, the connection information of the system interface, the passwords of each operator, or the like.

The operators of the automatic analyzer are persons of various levels from a beginner such as a doctor or a nurse who is not familiar with the operation of the automatic analyzer to a person in charge of the management of an analyzing room who is familiar with the operation of the automatic analyzer, or the like. Accordingly, in this embodiment, the operation functions accessible for these operators are divided into four levels from a level 1 to a level 4. Of these levels, the level 1 includes only the operation function which is required when a beginner such as a doctor or a nurse who usually does not operate the automatic analyzer uses the automatic analyzer, at the time of requiring an urgent inspection in the nighttime. The level 2 includes the operation function which is required in a hospital in the daytime or the like when an inspector operates the automatic analyzer and when a person in charge of the management of the analyzing room uses the automatic analyzer in order to check data. The level 3 includes, in addition to the operation functions of the levels 1 and 2, the operation function which is required when a skilled inspector changes the analysis parameter relating to the reagent etc. The level 4 includes, in addition to the operation functions of the levels 1 to 3, the operation function which is required when a service engineer or a person in charge of the management of the analyzing room uses the automatic analyzer. In other words, an operator of the level 4 can access all the operation functions of the automatic analyzer.

The relation between the operation screens capable of being displayed and the respective levels will be explained.

For example, in the case where a doctor or a nurse who usually scarcely operates the automatic analyzer uses the automatic analyzer at the time of urgent inspection, if an unnecessary screen is displayed, the urgent inspection of the sample can not be performed smoothly and further erroneous operation may be performed. In contrast, a person in charge of the management of the analyzing room is required to set the system parameter or the like. However, it is troublesome if the system parameter is changed easily by a person other than the person in charge of the management.

In view of such a matter, the screens accessible for persons of the respective levels except for the level 4 are restricted as follows.

As shown in FIG. 2, when an operator is one requiring only the operation function of the level 1, the controller of the automatic analyzer displays only the operation function screens of the routine screen A, that is, the patient sample request screen A1, the patient sample measuring result screen A2 and the initial setting screen A3 on the CRT display 100 serving as the display device. Thus, the operator is able to set the minimum input necessary for the analysis of a sample by using these operation function screens. For example, when an urgent inspection of a sample is necessary, a doctor or a nurse can request the automatic analyzer to perform the urgent inspection of the sample and obtain the measured result of the sample by means of the operation function of the level 1. In this case, the controller inhibits the usage of the operation functions of the levels 2 to 4.

When an operator is one requiring the operation function of the level 2, the controller of the automatic analyzer allows to display, in addition to the respective screens A1, A2 and A3 of the routine screen A, the reagent management screen B, the quality control screen C, the calibration screen D and the maintenance and inspection screen E1 of the utility screen E on the CRT display 100 so that the operator can access to these operation function screens. However, as described later, the operator of the level 2 is not allowed to use all operation functions of the maintenance and inspection screen E1 but is restricted to use a part thereof.

When an operator is one requiring the operation function of the level 3, the controller of the automatic analyzer allows to display, in addition to all the operation function screens of the routine screen A, the reagent management screen B, the quality control screen C and the calibration screen D, the maintenance and inspection screen E1 and the analysis parameter setting screen E2 of the utility screen E on the CRT display 100 so that the operator can access to these operation function screens. In other words, the operator of the level 3 is allowed to access to all the operation function screens of FIG. 2 except for the system parameter setting screen E3.

When an operator is one requiring the operation function of the level 4, the controller of the automatic analyzer allows to display, in addition to all the operation screens allowed to the operator of the level 3, the system parameter setting screen E3 of the utility screen E on the CRT display 100 so that the operator can access to all the operation function screens of FIG. 2. For example, although the controller of the automatic analyzer allows a person in charge of the management of the analyzing room to access to the system parameter setting screen E3, other persons are selectively allowed to access to the operation function screens of the levels 1 to 3 but can not change the system parameter.

The processing procedure for displaying the operation function screens in the automatic analyzer according to the embodiment will be explained with reference to FIG. 3.

In step 300, when the power supply of the automatic analyzer is turned on, the screen display processing is started. In step 310, the computer 50 serving as the controller shown in FIG. 1 displays an input screen for an operator name and a password on the CRT display 100. The operator name and the password are registered in the memory 56 in advance by using the system parameter setting screen E3.

In step 320, the computer 50 determines whether the operator name and the password have been inputted or not. If it is determined that the operator name and the password have been inputted, the process proceeds to step 330, while if it is determined that the operator name and the password have not been inputted, the process proceeds to step 340. The operator name and the password are not inputted in the case where the urgent inspection of a sample is required, for example. In other words, at the time of requiring the urgent inspection of a sample, the automatic analyzer is controlled so as to perform the minimum operation function (that is, the urgent inspection request of a sample and the display of the measured result thereof) due to the emergency of the inspection even if the operator name and the password are not inputted. Such an operation function corresponds to the level 1 of FIG. 2. The determination that the operator name and the password have not been inputted is made on the basis of the state where the password etc. were not inputted within a predetermined period or the state where an instruction button for accessing to the level 1 was pushed without inputting the password.

When the password etc. were not inputted in step 320, the controller displays the operation function selection screen described later with reference to FIG. 4 on the CRT display so that an operator can access only to an operation function selection button 110 for instructing the display of the operation function screen corresponding to the level 1. Accordingly, the analysis operation necessary for the urgent inspection of a sample can be executed by the automatic analyzer.

When the operator name and the password are inputted, the computer confirms the coincidence between the operator name and the password thus inputted and those registered in the memory 56 and then determines the level to be allowed for the operator, in step 330.

In step 340, the controller allows the operator to access to the operation function of the particular group in accordance with the level thus determined. That is, the computer 50 displays the operation function selection screen on the CRT display and controls the permission of the access to the selection buttons provided in corresponding to the respective operation function groups A to E, respectively, thereby to control the screen display so that the operator can open the operation function screen(s) corresponding to the level of the operator. The concrete contents of the screen display will be described later with reference to FIGS. 4 to 6.

Then, in step 350, the computer 50 accepts the input from the display screen or the key board 60 and executes the processing corresponding to the input. Thereafter, the process returns to step 310, whereat the computer 50 displays the input screen for a password etc. on the CRT display and waits for the next input.

Explanation will be made with reference to FIG. 4 as to an example of the display of the operation function screen which can be used for an operator allowed to use only the operation function of the level 1 in the automatic analyzer in FIG. 1.

Figure 4:
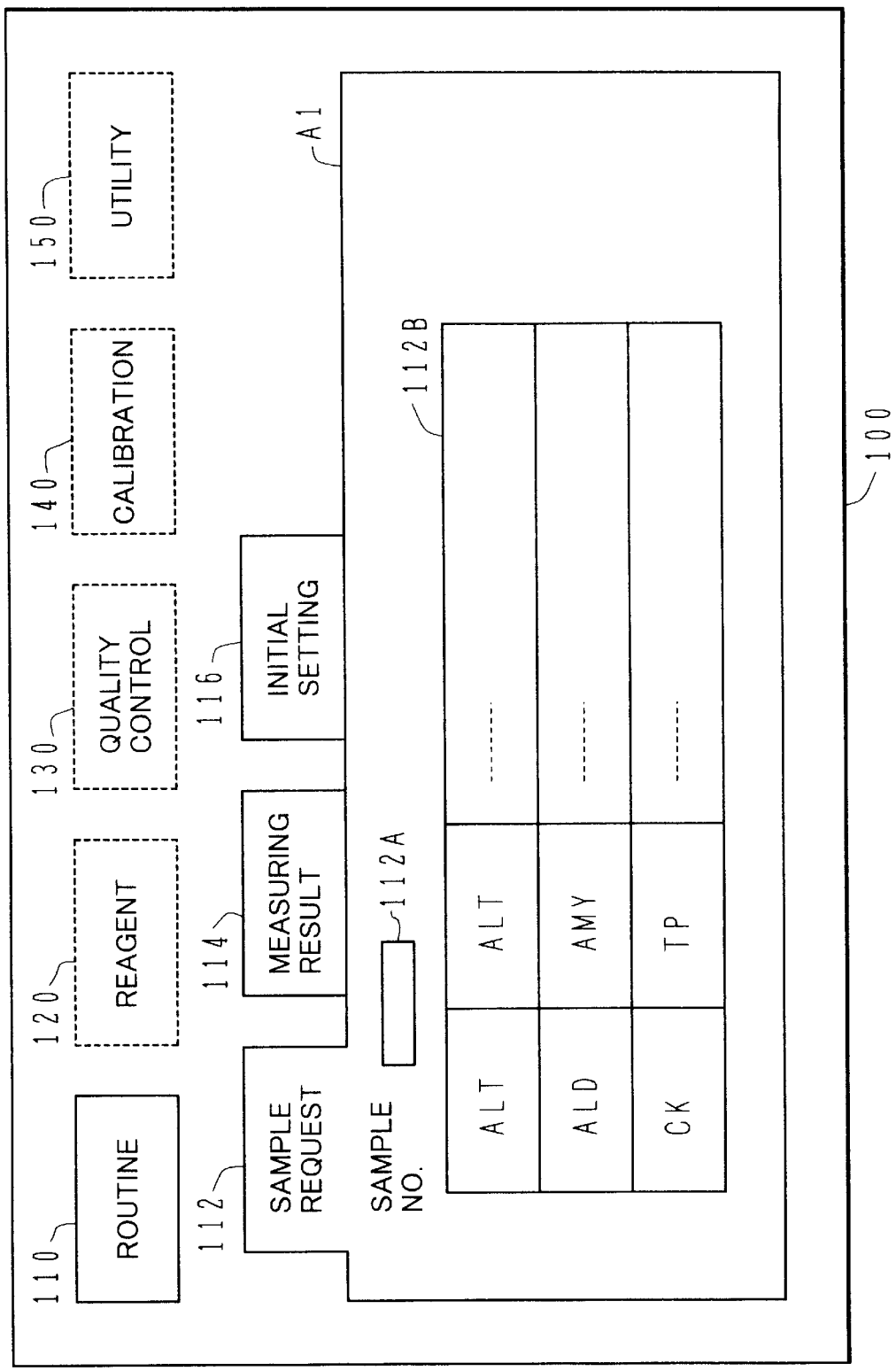
FIG. 4 is a diagram showing an example of the operation function screen in the automatic analyzer of FIG. 1 in the case where only the operation function of level 1 is allowed to be accessed.

When the process proceeds to step 340, a plurality of operation function selection buttons 110, 120, 130, 140 and 150 are displayed within the screen in FIG. 4 on the CRT display 100 but the individual operation function screens A1, A2 and A3 are not displayed yet. These operation function selection buttons are displayed in both cases where the operator inputted a password and where the operator did not input a password. However, the selection buttons accessible by the operator differ depending on the level of the operator. That is, when an operator is allowed to access only to the operation function of the level 1, since the operator is not allowed to access to the operation function groups B to E, the controller controls so that the operator can not access to the selection buttons 120, 130, 140, 150 corresponding to these groups.

In the screen shown in FIG. 4, an area for displaying the selection buttons corresponding to the plurality of the operation function groups is formed at the upper side, and an area for displaying the operation function screen corresponding to the selection button selected thereafter is formed at the lower side.

Of the five operation function selection buttons, the operation function selection button 110 is used for instructing to display the routine screen A. When the operation function selection button 110 is selected by using the key board 60, a mouse or the like, the patient sample request screen A1, the patient sample measuring result screen A2 and the initial setting screen A3 which are subclass operation function screens of the routine screen A can be displayed. The subclass operation function screens relating to the routine screen A are displayed in a hierarchy fashion or a multi-layer fashion. On the uppermost layer, there appears the patient sample request screen A1 which is most high in necessity for an operator and has a tag 112. On the secondary layer, the patient sample measuring result screen A2 which is secondarily high in necessity for an operator appears in a manner that this screen is hidden and only a tag 114 appears. On the lowermost layer, the initial setting screen A3 appear in a manner that this screen is hidden and only a tag 116 appears.

These subclass operation function screens are configured and selected in a form fashion. To be more concrete, when an operator selects one of the tags 112, 114, 116 respectively serving as the instruction buttons of the subclass operation function screens A1, A2, A3, the subclass operation function screen corresponding to the selected tag appears on the uppermost layer. In the state shown in FIG. 4, since the tag 112 is selected, the patient sample request screen A1 is displayed. Within the patient sample request screen A1, a column 112A for inputting the number of a sample (sample No.) and a plurality of inspection item selection buttons 112B are displayed. When the number of the inspection items are large, the list of these inspection items may be configured as a plural sheets of form.

Thus, at the time of the urgent inspection of a sample, even if an operator is a beginner of the automatic analyzer, the operator can easily operate the request for the inspection of a sample by merely inputting the sample No. into the column 112A and selecting the inspection item from the series of selection buttons 112B at every sample.

In FIG. 4, the button 120 is used for selecting the operation function group of the reagent management screen B, the button 130 is used for selecting the operation function group of the quality control screen C, the button 140 is used for selecting the operation function group of the calibration screen D and the button 150 is used for selecting the operation function group of the utility screen E. When an operator is allowed to access only to the operation function of the level 1, the operator is restricted not to access to the selection buttons 120, 130, 140, 150 other than the selection button 110. The operation function selection buttons corresponding to the groups which are allowed to be accessed in accordance with the level are displayed in different color from the operation function selection buttons corresponding to the groups which are not allowed to be accessed in accordance with the level. To be more concrete, when the level of an operator is level 1, the screen to be accessible and the screen not to be accessible are displayed in a different way visually in a manner that the non-accessible buttons 120 to 150 shown by dotted lines are displayed by gray and the accessible button 110 is displayed in a highlight manner, for example. For instance, even when an operator allowed to access only to the operation function of the level 1 tries to select the button 120, the reagent management screen B corresponding to the button 120 is not displayed.

In the case of performing the urgent analysis of a sample corresponding to the level 1, a nurse or a doctor who is a beginner as to the operation of the automatic analyzer at first input a sample No., then selects the inspection item, and inputs the sample setting position (the number of a sample disk and the position thereof) by using the patient sample request screen A1. When the analysis operation has been executed and the inspection of the sample has been completed, the operator can confirm the patient data after confirming the sample No. by using the patient sample measuring result screen A2. In this manner, since the urgent analysis of a sample can be performed by merely operating the patient sample request screen A1 and the patient sample measuring result screen A2, even a person who is not familiar with the operation of the automatic analyzer can easily operate the analyzer. Further, since the operator can not access to the unnecessary screens, the erroneous operation can be prevented, so that the reliability of the measured data can be improved.

Figure 5:
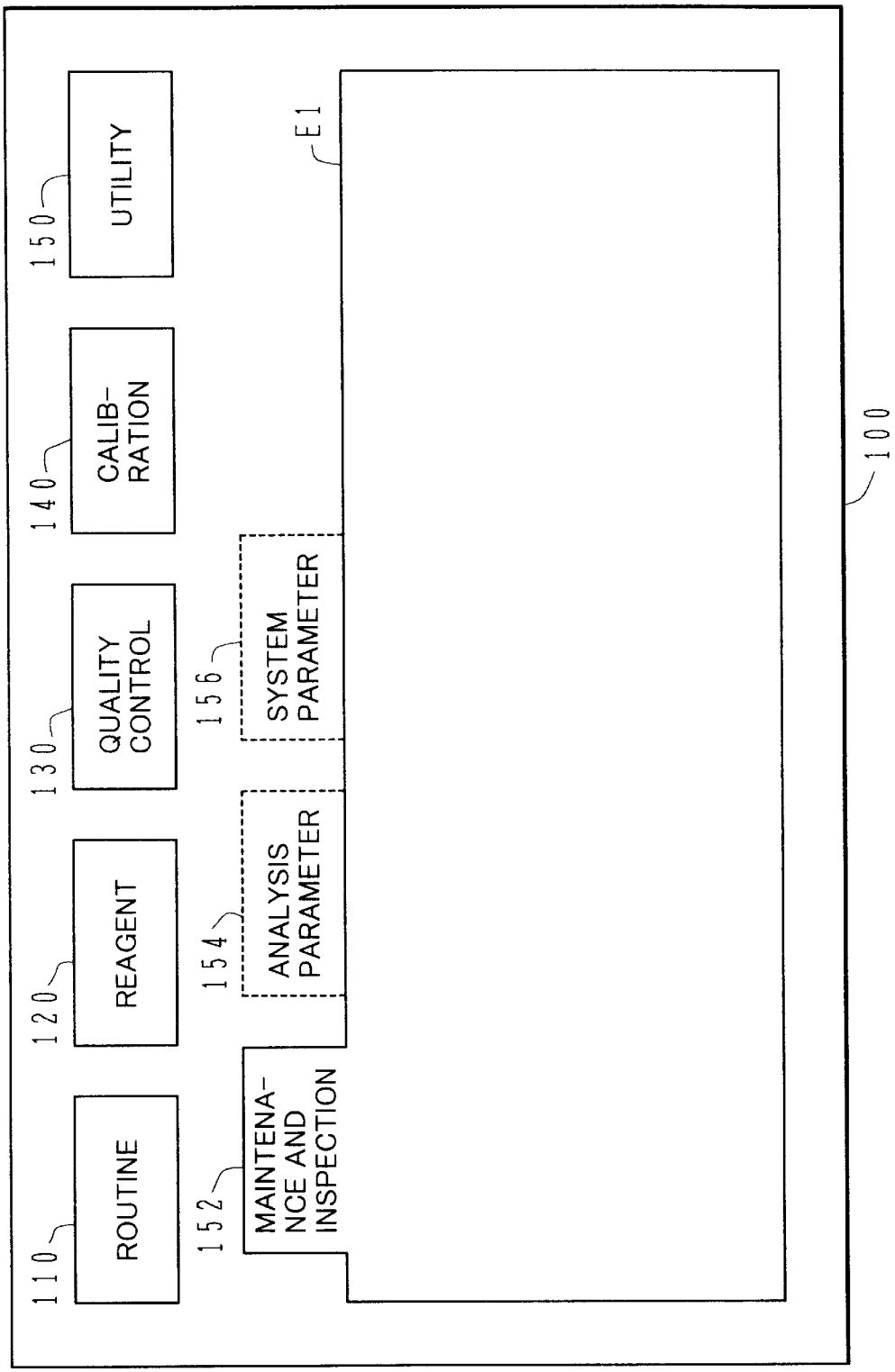
FIG. 5 is a diagram showing an example of the screen of the operation function in the automatic analyzer of FIG. 1 in the case where the operation function of level 2 is allowed to be accessed.

Explanation will be made with reference to FIG. 5 as to an example of the display of the operation function screen which can be used for an operator allowed to use the operation function of the level 2 in the automatic analyzer in FIG. 1.

When it is determined that the level to be allowed for the operator is the level 2 in step 330, the controller allows an operator to access to the reagent management screen B, the quality control screen C and the calibration screen D in addition to the subclass operation function screens A1, A2 and A3 of the routine screen A. Further, the operator is allowed to partially access to the maintenance and inspection screen E1 which is the subclass operation function screen of the utility screen E. However, the operator is not allowed to access to both the analysis parameter setting screen E2 and the system parameter setting screen E3. Accordingly, in step 340 of FIG. 3, the plurality of operation function selection buttons 110, 120, 130, 140 and 150shown at the upper area of the display screen of the CRT display 100 are displayed in a highlight manner representing to be accessible as shown by steady lines in FIG. 5.

Figure 3:
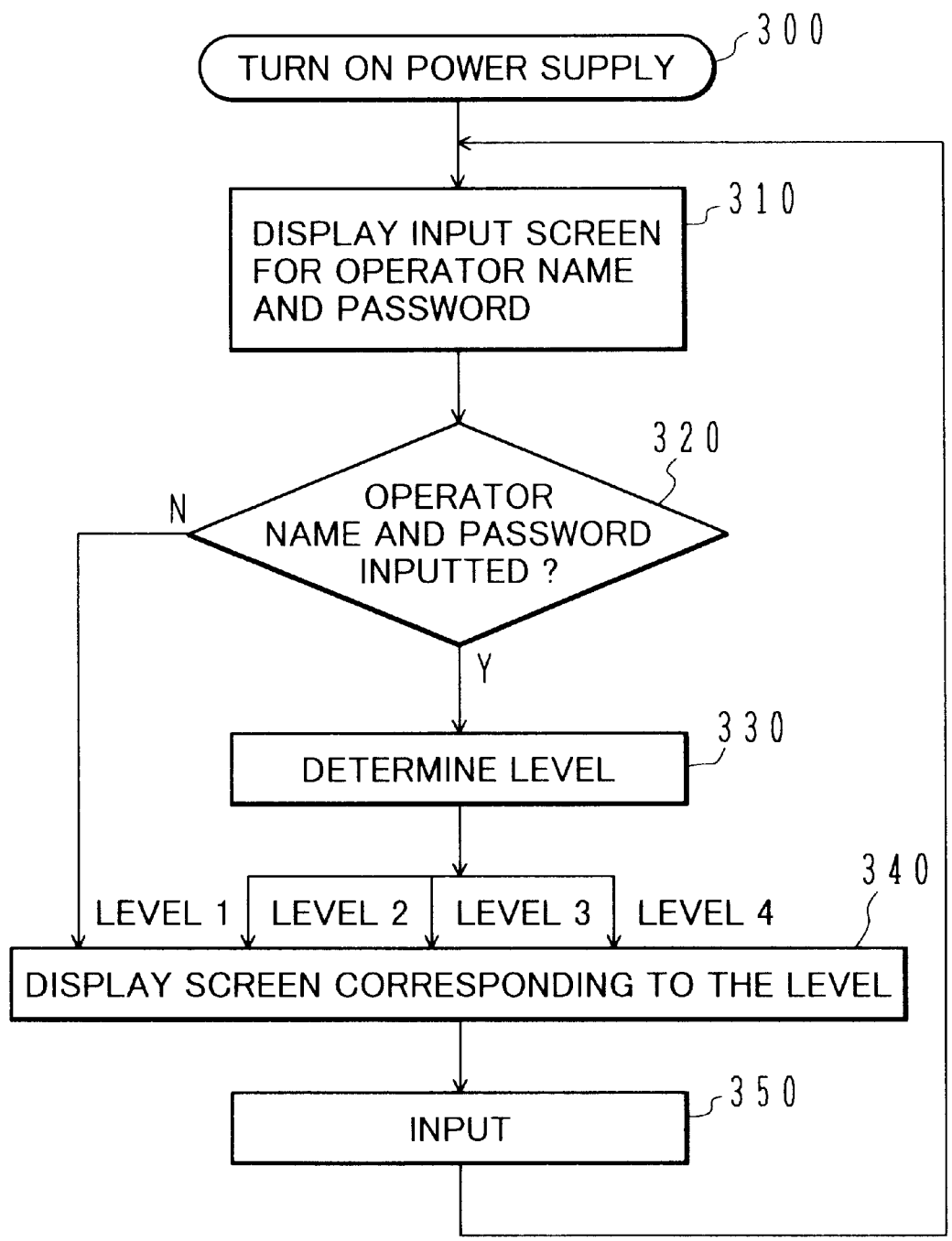
FIG. 3 is a flow chart showing the procedure for displaying the operation function screens in the automatic analyzer of FIG. 1.

In step 350 of FIG. 3, when the operation function selection button 150 corresponding to the operation function group of the utility screen E is selected, the plurality of the subclass operation function screens E1, E2, E3 relating to this selection button 150 are displayed in a hierarchy fashion or a multi-layer fashion. However, since the level of the operator is the level 2, the operator is allowed to access only to the maintenance and inspection screen E1 of the utility screen E. Thus, both the analysis parameter setting screen E2 and the system parameter setting screen E3 are hidden by the maintenance and inspection screen E1 except for tags 154 and 156 of these screens E2 and E3. In this level 2, the tag 152 of the maintenance and inspection screen E1 accessible by an operator is displayed in a highlight manner as shown by the steady line in FIG. 5, but the tag 154 of the analysis parameter setting screen E2 and the tag 156 of the system parameter setting screen E3 each not allowed to access are displayed by gray as shown by dotted lines in FIG. 5.

The utility screen E includes the plurality of the subclass operation function screens E1, E2, E3 which are arranged in a manner that the order of the multi-layers thereof is the order of the higher level of the subclass operation functions. To be more concrete, an operator who is allowed to access to the operation function of the level 2 can access to the maintenance and inspection screen E1 of the uppermost layer. An operator who is allowed to access to the operation function of the level 3 can access to the analysis parameter setting screen E2 of the secondary layer, and an operator who is allowed to access to the operation function of the level 4 can access to the system parameter setting screen E3 of the lowermost layer. An operator who is allowed to access to the operation function of the upper level 3 or 4 can open the corresponding lower operation function screen E2 or E3 on the uppermost layer by selecting the tag 154 or 156. In this manner, since an operator determined to be the level 2 can not access to both the analysis parameter setting screen E2 and the system parameter setting screen E3, the operator is prevented from erroneously changing the setting on the basis of these screens.

Figure 6:
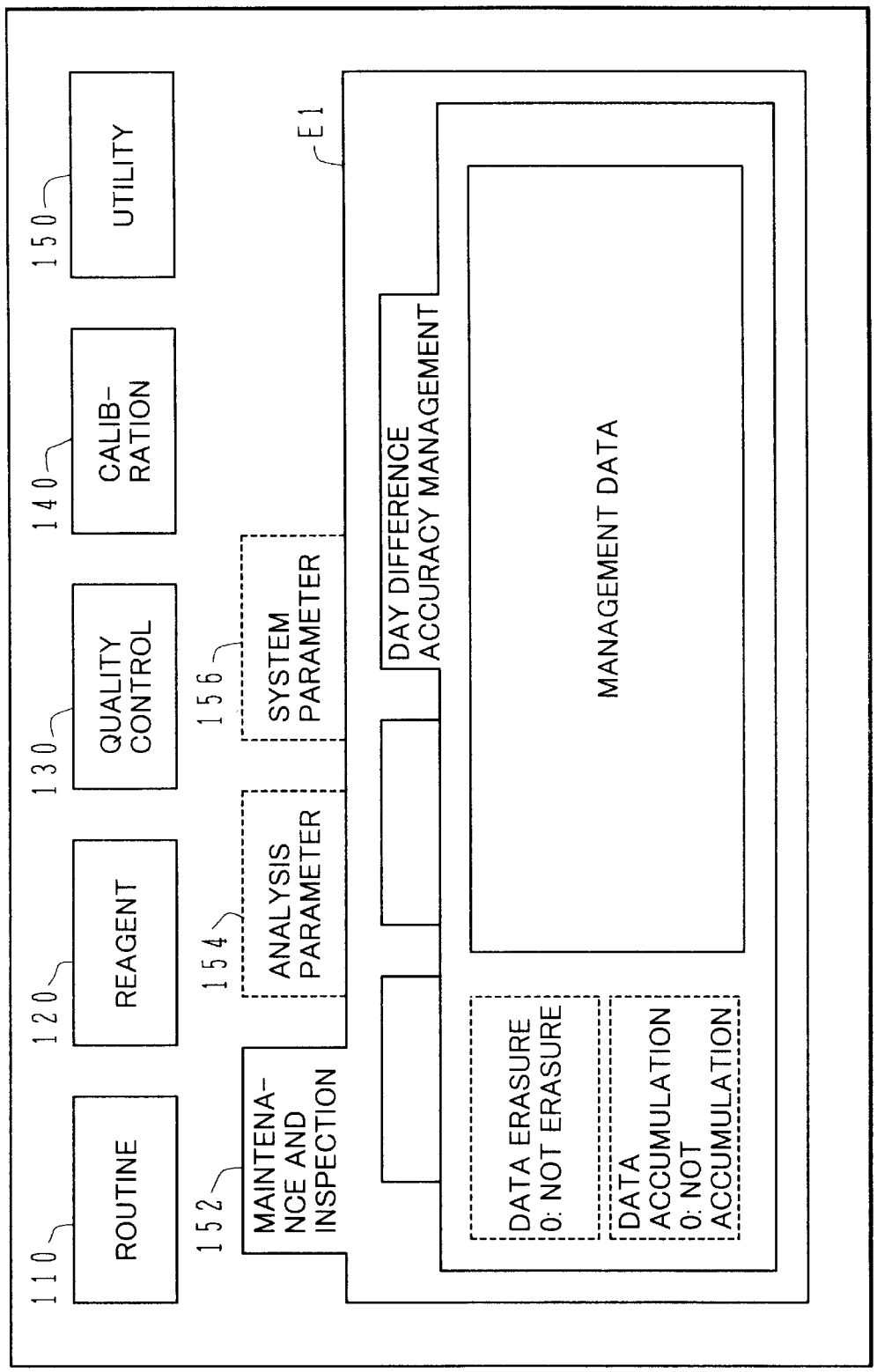
FIG. 6 is an explanatory diagram showing an example where the operation function are partially restricted in the case where the operation function of level 2 is allowed to be accessed in the automatic analyzer of FIG. 1.

Explanation will be made with reference to FIG. 6 as to an example of the operation function screens which are restricted to access when an operator allowed to access to the level 2 uses these screens. Although the maintenance and inspection screen E1 of the utility screen E can be accessed by the operators of the levels 2 to 4, the subclass operation functions of the maintenance and inspection screen E1 are classified into the operation functions accessible and not accessible by an operator depending on the level of the operator. To be more concrete, an operator of any of the levels 2 to 4 is allowed to access to and confirm the management data of the operation function of day difference management contained as one of the subclass operation functions of the maintenance and inspection screen E1. However, the erasure of the management data and the accumulation of the management data can not be accessed by an operator of the level 2 but are allowed to be accessed by an operator of the levels 3 and 4, whereby the management data is prevented from being erroneously erased by an operator of the level 2.

An operator who is allowed to access to the operation function of the level 3 can also manage the reagent, the calibration or the like. The setting operation of the analysis parameter or the like requires the special knowledge such as the designation of an amount of reagent, wavelength, light measurement point, designation of an alarm level, determination of the calibration result or the like, However, since such a setting operation can be performed only by the specialist, it can be prevented that the reliability of the measured data is degraded due to the access of an operator not having such a special knowledge.

A person in charge of the management of the analyzing room can set the level to be accessible by an operator by using the system parameter setting screen E3. Passwords allocated to the respective operators can be registered also by using the system parameter setting screen E3. The passwords are allocated only to persons of the levels 2 to 4 so as to prevent that other person illegally use the automatic analyzer. The password can be changed also by using the system parameter setting screen E3.

As described above, according to the embodiment of the present invention, since the levels of operators are set and the screens accessible by the operators are restricted depending on the levels in advance, even a beginner etc. of the automatic analyzer can easily operate the automatic analyzer and further the erroneous operation can be prevented. Since the automatic analyzer is provided with a user interface having such a screen configuration that the operation functions accessible by respective operators among the entire operation functions are clearly indicated and the plurality of the subclass operation function screens belonging to the operation function group selected by an operator are displayed in a hierarchy fashion or a multi-layer fashion, so that the operability and the reliability of the automatic analyzer can be improved.

What is claimed is:

1. An automatic analyzer for automatically analyzing a sample and obtaining a concentration of an inspection item of the sample, comprising:
    a memory for storing information of operation functions relating to said automatic analyzer divided into a plurality of groups;
    a controller for determining a level of access corresponding to a password having been inputted and allowing access to the operation function of one of said plurality of groups in accordance with the determined access level; and
    a display device for displaying a screen having an area for indicating operation function selection buttons corresponding to the respective groups of said operation functions and an area for indicating an operation function screen corresponding to a selected one of said operation function selection buttons,
    wherein said controller controls access of said operation function selection buttons that correspond to respective groups of said operation functions based on said determined access level for said respective groups of said operation functions so that said operation function selection buttons to which access is allowed are displayed differently from said operation function selection buttons to which access is not allowed by said controller, and
    wherein said one of said operation function selection buttons corresponding to said particular one of said plurality of groups for which access is allowed is displayed in a different color from that of said remaining ones of said operation function selection buttons corresponding to remaining ones of said operation function selection buttons for which access is not allowed,
    wherein when said password is not inputted after turning on of a power source of said automatic analyzer, said controller determines the level of access to be one in which access is allowed for ones of said operation function selection buttons corresponding to an operation function necessary for urgent analysis of a sample.

2. An automatic analyzer for automatically analyzing a sample and obtaining a concentration of an inspection item of the sample, comprising:
    a memory for storing information of operation functions relating to said automatic analyzer divided into a plurality of groups;
    a controller for determining a level of access corresponding to a password having been inputted and allowing access to the operation function of one of said plurality of groups in accordance with the determined access level; and
    a display device for displaying a screen having an area for indicating operation function selection buttons corresponding to the respective groups of said operation functions and an area for indicating an operation function screen corresponding to a selected one of said operation function selection buttons,
    wherein said controller controls access of said operation function selection buttons that correspond to respective groups of said operation functions based on said determined access level for said respective groups of said operation functions so that said operation function selection buttons to which access is allowed are displayed differently from said operation function selection buttons to which access is not allowed by said controller, and
    wherein in a case where one of said operation function selection buttons corresponding to said particular one of said plurality of groups for which access is allowed is selected, when there is a plurality of operation function screens relating to the selected one of said operation function selection buttons, said plurality of operation function screens are displayed in a multi-layer display,
    wherein when said password is not inputted after turning on of a power source of said automatic analyzer, said controller determines the level of access to be one in which access is allowed for ones of said operation function selection buttons corresponding to an operation function necessary for urgent analysis of a sample.

3. An automatic analyzer according to claim 2, wherein one of said plurality of operation function screens corresponding to the operation function of a basic operation is displayed as a top layer of the multilayer display.

4. An automatic analyzer for automatically analyzing a sample and obtaining a concentration of an inspection item of the sample, comprising:

a memory for storing information of operation functions relating to said automatic analyzer divided into a plurality of groups;

a controller for determining a level of access corresponding to a password having been inputted and allowing access to the operation function of one of said plurality of groups in accordance with the determined access level; and a display device for displaying a screen having an area for indicating operation function selection buttons corresponding to the respective groups of said operation functions and an area for indicating an operation function screen corresponding to a selected one of said operation function selection buttons, wherein said controller controls access of said operation function selection buttons that correspond to respective groups of said operation functions based on said determined access level for said respective groups of said operation functions so that said operation function selection buttons to which access is allowed are displayed differently from said operation function selection buttons to which access is not allowed by said controller, and wherein when said password is not inputted after turning-on of a power source of said automatic analyzer, said controller determines the level of access to be one in which access is allowed for ones of said operation function selection buttons corresponding to an operation function necessary for urgent analysis of a sample.

* * * * *